United States Patent
Cho et al.

(10) Patent No.: US 10,085,717 B2
(45) Date of Patent: Oct. 2, 2018

(54) ULTRASONIC PROBE

(71) Applicant: SAMSUNG ELECTRONICS CO., LTD., Suwon-si (KR)

(72) Inventors: Kyungil Cho, Seoul (KR); Jong Keun Song, Yongin-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 551 days.

(21) Appl. No.: 14/808,326

(22) Filed: Jul. 24, 2015

(65) Prior Publication Data

US 2016/0041129 A1    Feb. 11, 2016

(30) Foreign Application Priority Data

Aug. 8, 2014  (KR) .................. 10-2014-0102545

(51) Int. Cl.
    *A61B 8/00*    (2006.01)
(52) U.S. Cl.
    CPC ............ *A61B 8/4444* (2013.01); *A61B 8/546* (2013.01); *A61B 8/4281* (2013.01)

(58) Field of Classification Search
    CPC .......... A61B 8/546; A61B 8/44; A61B 8/4444
    See application file for complete search history.

(56) References Cited

U.S. PATENT DOCUMENTS

| | | | | |
|---|---|---|---|---|
| 5,560,362 A | * | 10/1996 | Sliwa, Jr. ............... | A61B 8/546 600/439 |
| 2008/0188755 A1 | * | 8/2008 | Hart ........................ | A61B 8/00 600/459 |
| 2013/0286593 A1 | * | 10/2013 | Cho ...................... | B06B 1/0292 361/707 |

* cited by examiner

*Primary Examiner* — Joel Lamprecht
(74) *Attorney, Agent, or Firm* — Sughrue Mion, PLLC

(57) ABSTRACT

An ultrasonic probe includes: a housing having an opening provided at a first end portion of the housing; a transducer provided in a position corresponding to the opening and configured to generate ultrasonic waves; a heat spreader provided underneath the transducer; and a printed circuit board (PCB) disposed between the transducer and the heat spreader, wherein the heat spreader includes: a body portion configured to absorb heat from the transducer; and a coupling portion that is formed at a side portion of the body portion and coupled to the housing.

22 Claims, 8 Drawing Sheets

ULTRASONIC PROBE

CROSS-REFERENCE TO RELATED APPLICATION

This application claims priority from Korean Patent Application No. 10-2014-0102545, filed on Aug. 8, 2014 in the Korean Intellectual Property Office, the disclosure of which is incorporated herein by reference in its entirety.

BACKGROUND

1. Field

Apparatuses consistent with exemplary embodiments relate to an ultrasonic probe for an ultrasonic diagnostic instrument for diagnosing a disease.

2. Description of the Related Art

Ultrasonic diagnostic instruments are instruments that radiate ultrasonic waves toward a target part inside an object from a surface of the object and obtain an image regarding a fault of a soft tissue or a blood flow of the soft tissue in a non-invasive manner by receiving reflected ultrasonic-wave echo signals.

In comparison with other image diagnostic instruments, such as X-ray diagnostic instruments, computerized tomography (CT) scanners, magnetic resonance image (MRI) diagnostic instruments, and nuclear medicine diagnostic instruments, ultrasonic diagnostic instruments are small-sized and cheap, can display an image in real time, and have high safety due to lack of radiation exposure. Thus, ultrasonic diagnostic instruments are widely used in heart, abdominal, urinary, and ob-gyn diagnoses.

An ultrasonic diagnostic instrument includes an ultrasonic probe that radiates ultrasonic waves onto the object and receives ultrasonic echo signals reflected from the object so as to obtain an image inside the object.

In general, a piezoelectric material that converts electrical energy into mechanical vibration energy and generates ultrasonic waves, is widely used to form a transducer that generates ultrasonic waves in the ultrasonic probe.

A capacitive micromachined ultrasonic transducer (hereinafter referred to as a "cMUT") that is a new concept of transducer has been recently developed.

In recent years, research on and manufacturing transducers of two-dimensional (2D) arrays have been briskly conducted. The cMUT is appropriate to manufacture a transducer of a 2D array and thus facilitates development of a multi-channel transducer.

However, when the number of transducer channels is small, a caloric value generated in an electric circuit for driving the probe is merely 1 W and can be naturally discharged through a case of the probe. However, as the transducer has multi-channels, the caloric value is increased to 7 W and thus the development of technology for heat-dissipation and cooling of the ultrasonic probe is required.

SUMMARY

Therefore, one or more exemplary embodiments provide an ultrasonic probe having an improved structure in which heat generated in the ultrasonic probe can be effectively dissipated to the outside.

The exemplary embodiments also provide an ultrasonic probe having an improved structure in which stability and manufacturing facilitation of the ultrasonic probe can be improved.

Additional aspects of the inventive concept will be set forth in part in the description which follows and, in part, will be obvious from the description, or may be learned by practice of the inventive concept.

In accordance with an aspect of an exemplary embodiment, there is provided an ultrasonic probe including: a housing having an opening formed in one side of the housing; a transducer that is formed in a position corresponding to the opening and generates ultrasonic waves; a heat spreader formed under the transducer; and a printed circuit board (PCB) disposed between the transducer and the heat spreader, wherein the heat spreader may include: a body portion that absorbs heat from the transducer; and a coupling portion that is formed in a side of the body portion and is coupled to one side in an inside of the housing.

The ultrasonic probe may further include a support portion that is formed in an upper portion of the coupling portion at one side of the body portion and supports the PCB.

The housing may include: an upper housing having the opening formed therein; and a lower housing coupled to the upper housing. The coupling portion may be formed to be coupled to one side in an inside area of the upper housing.

The upper housing may further include a hanging portion formed in one side in the inside of the upper housing to be in contact with a top surface of the PCB.

The hanging portion may be formed in a position corresponding to an edge area of the PCB and may have a stepped shape.

The heat spreader may further include protrusions that protrude from a top surface of the body portion upward, and the PCT has a connection hole formed in a position corresponding to the protrusions, and the protrusions may be inserted into the connection hole.

The heat spreader may be formed so that the protrusions are spaced a predetermined distance from a lower portion of the transducer.

Thermal grease or a phase change material may be provided between the protrusions and the transducer.

The ultrasonic probe may further include: a heat sink that is disposed at one side of a lower portion of the lower housing and dissipates transferred heat to the outside; and a heat pipe having one side connected to the heat spreader and the other side connected to the heat sink and transferring heat.

The ultrasonic probe may include: at least one heat-dissipation plate coupled to a first side of the heat spreader; and at least one vertical board that is disposed in an inside of the heat-dissipation plate and coupled to a second side of the heat spreader.

The ultrasonic probe may further include a connection member that electrically connects the PCB and the at least one vertical board.

The connection member may be provided as a flexible PCB (FPCB).

The heat-dissipation plate may include: a heat-dissipation plate body that is disposed spaced a predetermined distance from the at least one vertical board; and a heat-dissipation plate coupling portion that extends from both sides of the heat-dissipation plate body upward and is coupled to the second side of the heat spreader. The heat-dissipation plate body may be formed so that a top end of the heat-dissipation plate body is disposed in a lower position than the connection member.

The heat-dissipation plate coupling portion may be disposed so that a top end of the heat-dissipation plate coupling portion is formed in a rounded shape.

The ultrasonic probe may further include a cable connection portion which is connected to a lower end of the housing and has a space formed therein. The cable connection portion may include a strain relief.

The strain relief may be connected to the heat sink and may include a thermally conductive material.

In accordance with an aspect of another exemplary embodiment, there is provided an ultrasonic probe including: a housing having an opening formed in one side of the housing; a transducer that is formed in a position corresponding to the opening and generates ultrasonic waves; a heat spreader formed under the transducer so as to absorb heat generated in the transducer; at least one heat-dissipation plate coupled to a first side of the heat spreader; and at least one vertical board that is disposed in an inside of the heat-dissipation plate and coupled to a second side of the heat spreader.

The ultrasonic probe may further include a connection member that electrically connects the PCB and the at least one vertical board, wherein the heat-dissipation plate may include: a heat-dissipation plate body disposed spaced a predetermined distance from the at least one vertical board; and a heat-dissipation plate coupling portion that extends from both sides of the heat-dissipation plate body upward and is coupled to the second side of the heat spreader. The heat-dissipation plate body may be formed so that a top end of the heat-dissipation plate body is disposed in a lower position than the connection member.

The heat-dissipation plate coupling portion may be disposed so that a top end of the heat-dissipation plate coupling portion is formed in a rounded shape.

The ultrasonic probe may further include a cable connection portion which is connected to a lower end of the housing and has a space formed therein. The cable connection portion may include a strain relief.

The ultrasonic probe may further include: a heat sink that is disposed at one side of a lower portion of the lower housing and dissipates transferred heat to the outside; and a heat pipe having one side connected to the heat spreader and the other side connected to the heat sink and transferring heat.

The strain relief may be connected to the heat sink and may include a thermally conductive material.

BRIEF DESCRIPTION OF THE DRAWINGS

The above and/or other aspects of the disclosure will become apparent and more readily appreciated from the following description of the exemplary embodiments, taken in conjunction with the accompanying drawings of which.

DETAILED DESCRIPTION

Reference will now be made in detail to exemplary embodiments, examples of which are illustrated in the accompanying drawings, wherein like reference numerals refer to like elements throughout.

Hereinafter, the exemplary embodiments will be described in more detail with reference to the accompanying drawings.

Figure 1:
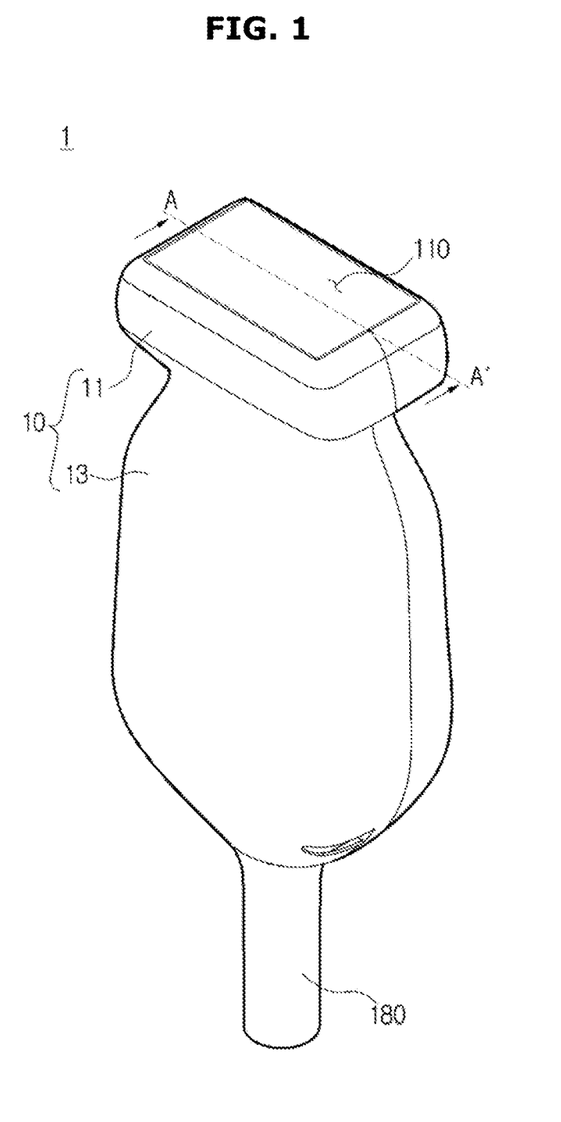
FIG. 1 is a perspective view of an exterior of an ultrasonic probe in accordance with an exemplary embodiment.

FIG. 1 is a perspective view of an exterior of an ultrasonic probe in accordance with an exemplary embodiment.

Figure 2:
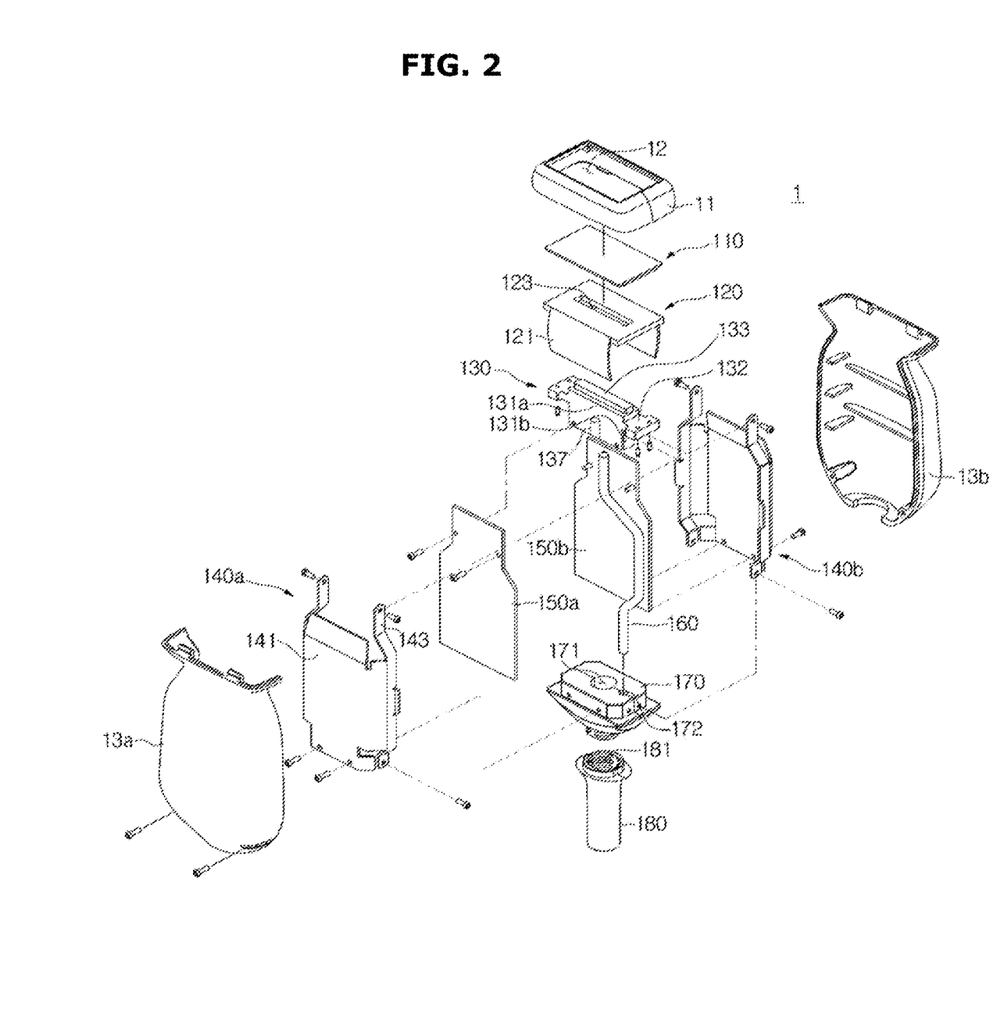
FIG. 2 is an exploded perspective view of the ultrasonic probe illustrated in FIG. 1.

Referring to FIGS. 1 and 2, an ultrasonic probe 1 may include a housing 10 that forms an exterior, and a transducer 110 that generates ultrasonic waves in the housing 10.

The housing 10 may include an upper housing 11 and a lower housing 13. The upper housing 11 and the lower housing 13 may be coupled to each other to form an internal space. The upper housing 11 and the lower housing 13 may be coupled to each other to form an exterior in which the transducer 110, a heat spreader 130, and other electronic apparatus components of the ultrasonic probe 1 are disposed therein.

The transducer 110 may be disposed in an upper portion, i.e., a first end portion, of the housing 10. The housing 10 may be disposed in a shape in which one side of the upper portion of the housing 10 is opened so that a part of the transducer 110 may be exposed.

A cable connection portion 180 may be disposed in a lower portion, i.e., a second end portion, of the housing 10. The cable connection portion 180 may be coupled to a bottom surface, i.e., a second surface, of a lower housing 13. A space 181, in which a cable is disposed, may be formed in the cable connection portion 180. The space 181 may be formed to be connected to a communication hole 171 of a heat sink 170.

FIG. 2 is an exploded perspective view of the ultrasonic probe of FIG. 1.

Referring to FIG. 2, the ultrasonic probe 1 may further include the heat spreader 130 that absorbs heat generated in the transducer 110.

An opening 12 may be formed in an upper housing 11. The opening 12 may be formed in one side of the upper portion of the upper housing 11 and may serve as a path through which ultrasonic waves generated in the transducer 110 go. The opening 12 may be formed in a shape corresponding to the transducer 110.

A hanging portion 15 may be formed in an inside of the upper housing 11. The hanging portion 15 may be formed in a position in which the position of a printed circuit board (PCB) 120 that will be described later may be fixed. The hanging portion 15 may be formed in a position that faces an edge area of the PCB 120 in the inside of the upper housing 11. The hanging portion 15 may be in contact with one side of an upper portion of the PCB 120 and may cause the position of the PCB 120 to be fixed without being coupled to other configuration. The hanging portion 15 may be formed in a stepped shape in the inside of the upper housing 11.

The lower housing 13 may include a front housing 13a and a rear housing 13b. The front housing 13a and the rear housing 13b may be formed in a shape symmetrical with each other. The front housing 13a and the rear housing 13b may be coupled to each other to form an internal space in which a heat-dissipation plate 140 and a vertical board 150 that will be described later may be disposed.

Figure 3:
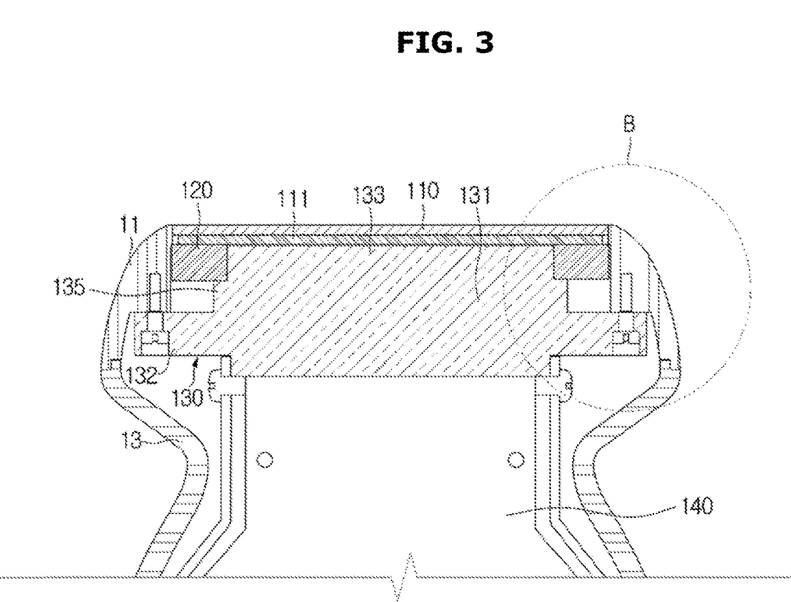
FIG. 3 is a cross-sectional view of the ultrasonic probe taken along a line A-A' of FIG. 1.
Figure 4:
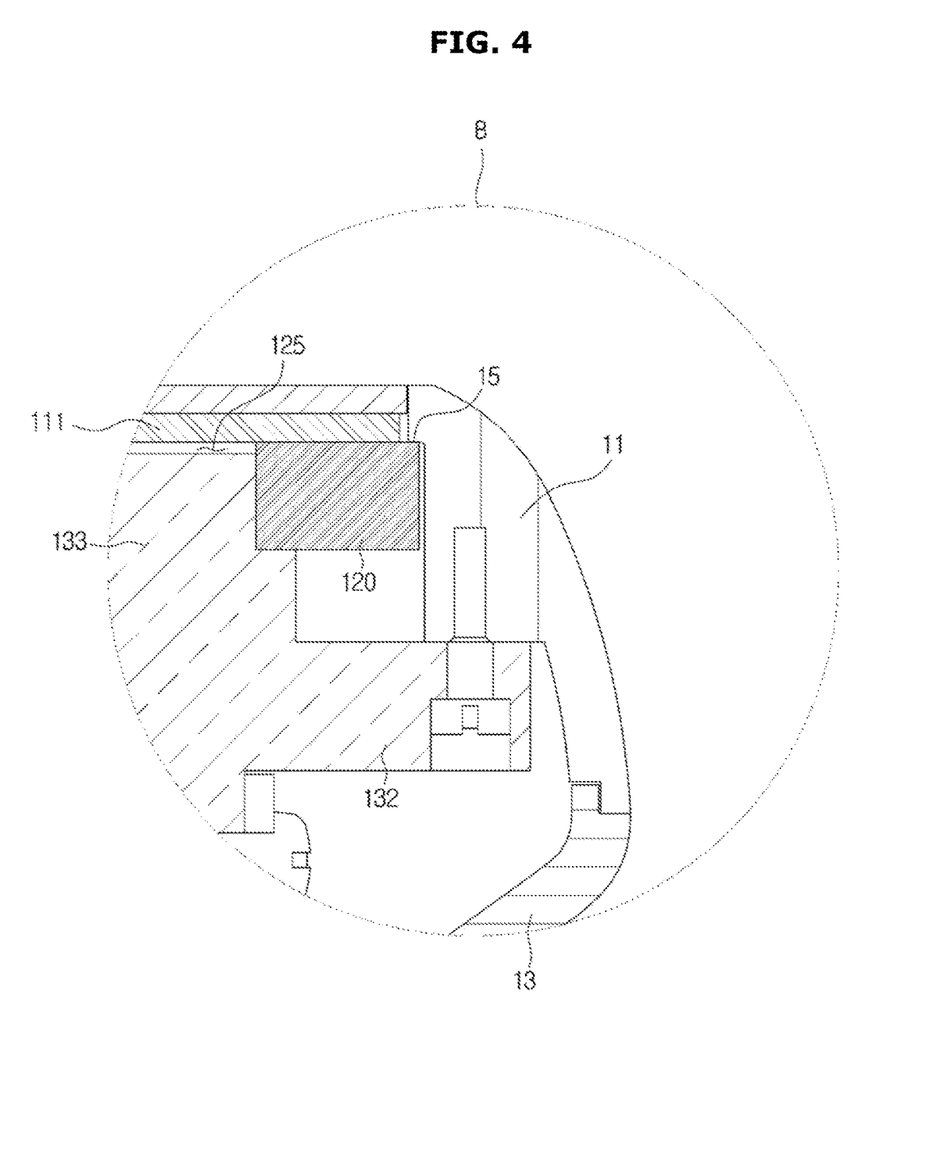
FIG. 4 is an enlarged view of a portion B of FIG. 3.

FIG. 3 is a cross-sectional view of the ultrasonic probe taken along a line A-A' of FIG. 1, and FIG. 4 is an enlarged view of a portion B of FIG. 3.

Referring to FIGS. 2 through 4, the transducer 110 may be disposed to face the opening 12 in the inside of the housing 10. In an embodiment of the transducer 110, a magnetostrictive ultrasonic transducer that uses a magnetostrictive effect of a magnetic material mainly used in the ultrasonic probe 1, or a piezoelectric ultrasonic transducer that uses a piezoelectric effect of a piezoelectric material may be used as the transducer 110. Alternatively, a capacitive micromachined ultrasonic transducer (hereinafter abbreviated to a "cMUT") that receives/transmits ultrasonic waves using vibration of several hundreds or thousands of micromachined thin films, may be used as the transducer 110. Hereinafter, a case where the cMUT is used as the transducer 110, will be assumed and described. However, the transducer 110 applied to the ultrasonic probe 1 according to the spirit of the inventive concept is not limited to the cMUT.

Integrated circuits (ICs) 111 may be installed on a bottom surface, i.e., a second surface, of the transducer 110. A cMUT array may be generally bonded to the ICs 111, such as application specific integrated circuits (ASICs), using a flip chip bonding method.

The ultrasonic probe 1 may further include a printed circuit board (PCB) 120. The PCB 120 may be disposed in a lower portion, i.e., a second end portion, of the transducer 110. Signal lines of the ASICs 111 to which the cMUT array is bonded, may be bonded to the PCB 120 using a wire bonding method.

A connection hole 123 may be formed in the PCB 120. The connection hole 123 may be configured so that the ICs 111 installed on the bottom surface, i.e., the second surface, of the transducer 110 may be exposed. The connection hole 123 may be formed so that one side of the heat spreader 130 is inserted into the connection hole 123 and the heat spreader 130 may absorb heat generated in the transducer 110.

The PCB 120 may further include a connection member 121. The connection member 121 may extend from one side of the PCB 120 and may be electrically connected to the vertical board 150 that will be described later. The connection member 121 may be formed of a flexible PCB (FPCB) 121 that is flexible.

The heat spreader 130 may be disposed in a lower portion of the transducer 110. The heat spreader 130 may be configured to absorb heat generated in the transducer 110. The heat spreader 130 may include a metal having excellent thermal conductivity.

The heat spreader 130 may include a body portion 131 and a coupling portion 132.

The body portion 131 may be formed in a hexahedral shape. The body portion 131 may be provided to have a uniform volume so as to absorb heat from the transducer 110.

The coupling portion 132 may be formed at one side of the body portion 131. The coupling portion 132 may be formed to protrude from both sides of the body portion 131. The coupling portion 132 may be formed to be coupled to an inside surface of the upper housing 11. The coupling portion 132 may be coupled to the inside surface of the upper housing 11 and may couple the heat spreader 130 and the upper housing 11.

In one embodiment, the PCB 120 may be inserted into and disposed in a space formed between the body portion 131 and the upper housing 11. Thus, the PCB 120 may be fixedly installed in a predetermined position without being separately coupled to the upper housing 11 and the heat spreader 130.

The heat spreader 130 may further include protrusions 133. The protrusions 133 may be formed to protrude from a top surface of the body portion 131 upward. The protrusions 133 may be formed to correspond to the connection hole 123 of the PCB 120. The protrusions 133 may be inserted into the connection hole 123 so that the position of the PCB 120 may be fixed. Also, the protrusions 133 may be formed to be inserted into the connection hole 123 and to absorb heat from the transducer.

The protrusions 133 may be formed spaced a predetermined distance from a bottom surface, i.e., a second surface, of the transducer 110. A heat transfer medium 125 may be disposed in the space between the protrusions 133 and the transducer 110. The heat transfer medium 125 may be thermal grease that is a thermal medium having good thermal conductivity, or a phase change material.

As illustrated in FIG. 4, the heat spreader 130 may further include a support portion 135. The support portion 135 may be formed to extend from a border between the body portion 131 and the coupling portion 132 along the body portion 131 upward. The support portion 135 may support the PCB 120. The support portion 135 may support the PCB 120 so that the PCB 120 may be disposed at a predetermined height. The support portion 135 may be formed at both sides of the body portion 131 together with the coupling portion 132.

The heat spreader 130 may further include an insertion groove 137. The insertion groove 137 may provide a space in which a heat pipe 160 that will be described later may be inserted. The depth of the insertion groove 137 formed in the heat spreader 130 may reach a surface on which the heat spreader 130 is in thermal contact with the transducer 110 so that heat may be effectively transferred from the heat spreader 130 to the heat pipe 160.

Figure 5:
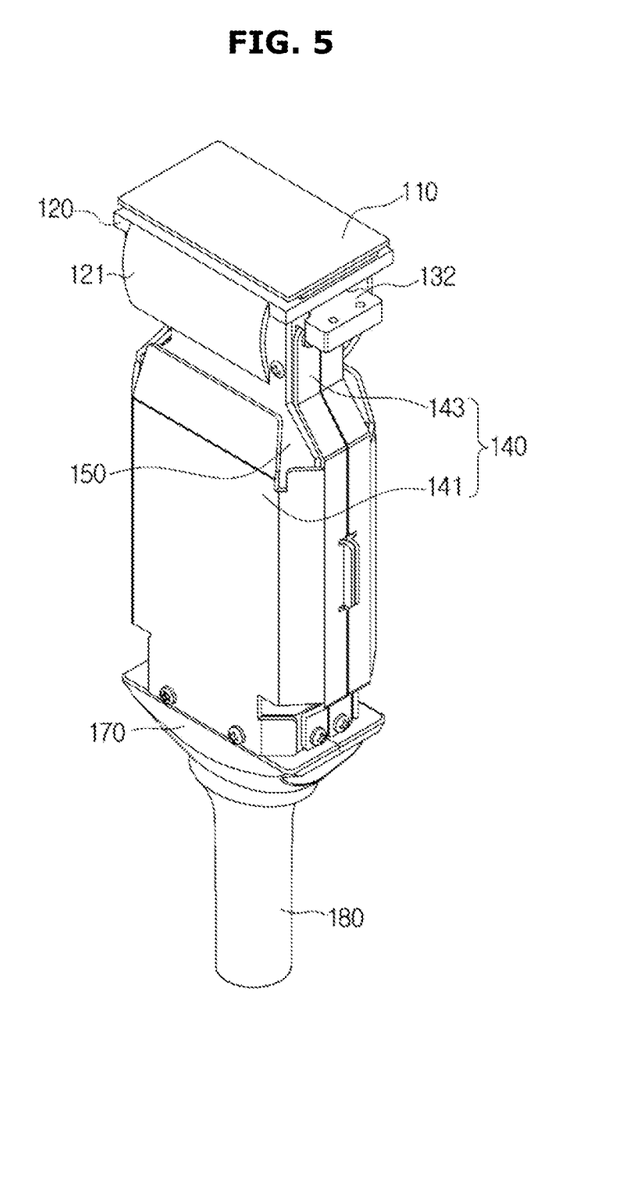
FIG. 5 is a perspective view of a structure of the ultrasonic probe in which a housing is removed from the ultrasonic probe of FIG. 1
Figure 6:
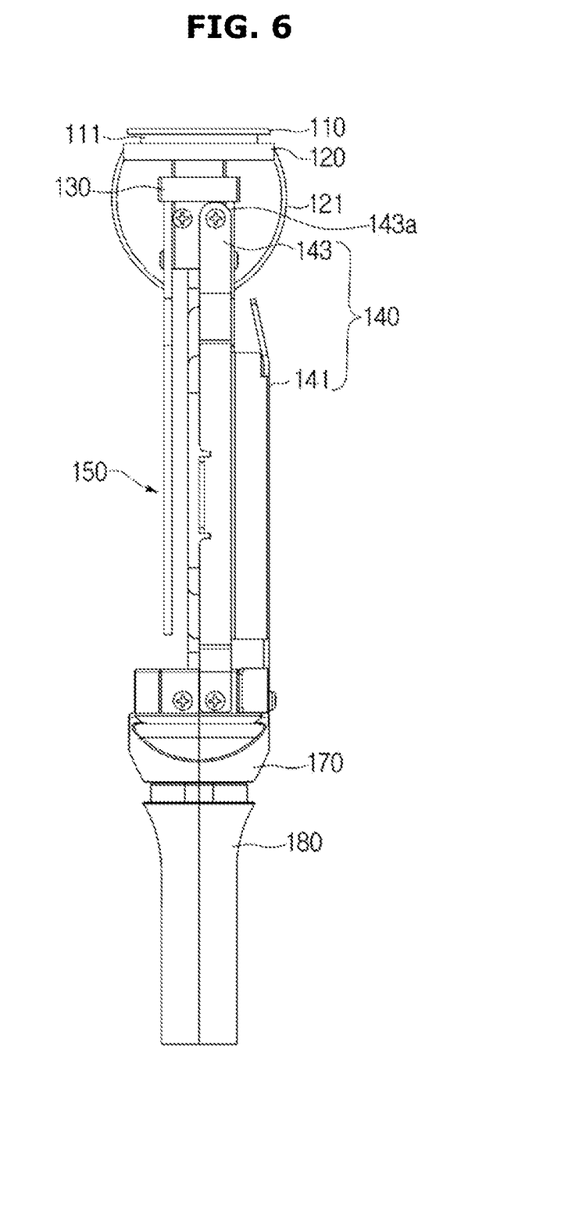
FIG. 6 is a side view of the ultrasonic probe in which one side of a heat-dissipation plate is removed from the ultrasonic probe of FIG. 5.
Figure 7:
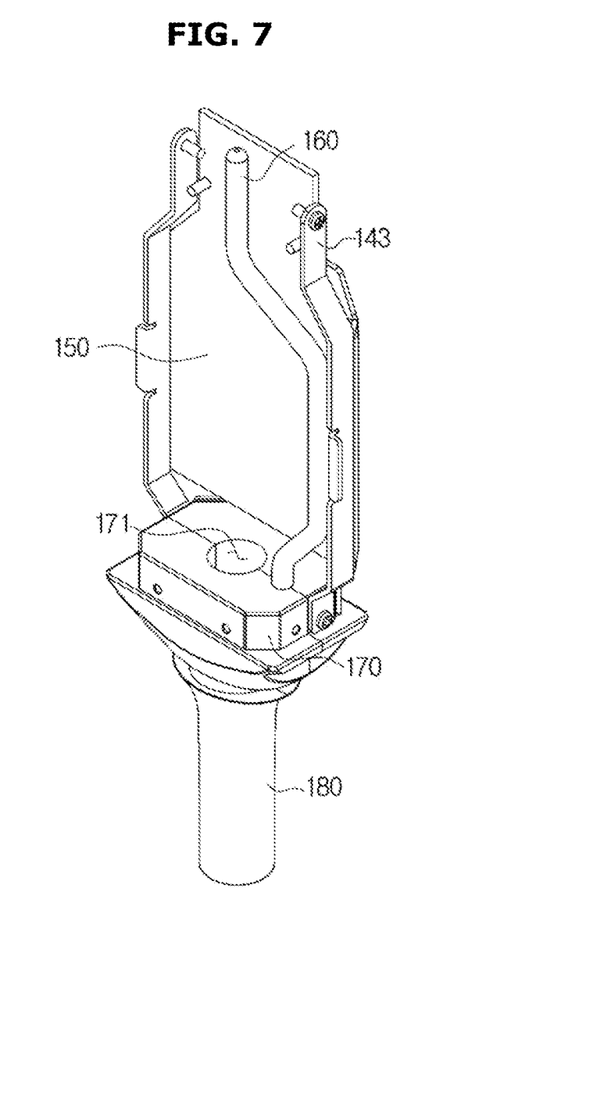
FIG. 7 is a perspective view of a structure of an ultrasonic probe in which a front housing, a first heat-dissipation plate, and a first vertical board are removed from the ultrasonic probe of FIG. 1.

FIG. 5 is a perspective view of a structure of the ultrasonic probe in which a housing is removed from the ultrasonic probe of FIG. 1, and FIG. 6 is a side view of the ultrasonic probe in which one side of a heat-dissipation plate is removed from the ultrasonic probe of FIG. 5, and FIG. 7 is a perspective view of a structure of an ultrasonic probe in which a front housing, a first heat-dissipation plate, and a first vertical board are removed from the ultrasonic probe of FIG. 1.

Referring to FIGS. 5 through 7, the ultrasonic probe 1 may further include a heat-dissipation plate 140. The heat-dissipation plate 140 may be formed to be connected to the heat spreader 130. The heat-dissipation plate 140 may serve as a path through which heat of the heat spreader 130 is transferred to an outside of the ultrasonic probe 1.

The heat-dissipation plate 140 may include a first heat-dissipation plate 140a and a second heat-dissipation plate 140b. The first heat-dissipation plate 140a and the second heat-dissipation plate 140b may be disposed in front of and behind the lower housing 13 in an inside area of the lower housing 13.

The heat-dissipation plate 140 may include a heat-dissipation plate body 141 and a heat-dissipation plate coupling portion 143.

The heat-dissipation plate body 141 may be formed spaced a predetermined distance from the lower housing 13 inward. The heat-dissipation plate body 141 may have a front side and both sides that are bent from the front side. One side of a lower portion, i.e., a second end portion, of the heat-dissipation plate body 141 may be coupled to the heat sink 170 that will be described later. Thus, the heat-dissipation plate body 141 may transfer heat that goes from the heat spreader 130 toward the heat-dissipation plate coupling portion 143, to the heat sink 170.

In one embodiment, a top end, i.e., a first end, of the heat-dissipation plate body 141 may be disposed in a lower position than the connection member 121. The top end, i.e., the first end, of the heat-dissipation plate body 141 may be disposed in a lower position than a position in which the connection member 121 is coupled to the vertical board 150 so that the heat-dissipation plate body 141 may be prevented from being disposed in a position in which the connection member 121 and the heat-dissipation plate 140 overlap.

The heat-dissipation plate coupling portion 143 may be connected to the heat spreader 130 so as to receive heat from the heat spreader 130. The heat-dissipation plate coupling portion 143 may be formed to extend from one side of the heat-dissipation plate body 141 upward. The heat-dissipation plate coupling portion 143 may extend from both sides of the heat-dissipation plate body 141 upward and may be coupled to a second side 131b of the heat spreader 130. The second side 131b may be defined as both sides of the heat spreader 130.

The heat-dissipation plate coupling portion 143 may be coupled to the second side 131b and may prevent the vertical board 150 that will be described later from being coupled to the same side of the heat spreader 130. Thus, a space inside the ultrasonic probe 1 may be effectively utilized. Also, physical interference with other configurations formed in the ultrasonic probe 1 may be prevented so that the reliability of a product may be improved.

In an embodiment, a top end, i.e., a first end, of the heat-dissipation plate coupling portion 143 may be formed in a rounded shape. Thus, even when the position of the heat-dissipation plate 140 is moved, the heat-dissipation plate coupling portion 143 may be rotated within a predetermined angle while it is coupled to the heat spreader 130.

The vertical board 150 may be disposed in the heat-dissipation plate 140. One side of an upper portion, i.e., a first end portion, of the vertical board 150 may be coupled to the heat spreader 130. The one side of the upper portion of the vertical board 150 may be coupled to a first side 131a of the heat spreader 130. The first side 131a may be defined as one of a front side and a rear side of the heat spreader 130.

As described above, the vertical board 150 may be coupled to a side of the heat spreader 130 that is different from the heat-dissipation plate 140. Thus, the vertical board 150, the heat-dissipation plate 140, and the connection member 121 may be disposed so that physical interference therewith may not occur in the ultrasonic probe 1.

The vertical board 150 may include a first vertical board 150a and a second vertical board 150b. The first vertical board 150a may be disposed in an inside of the first heat-dissipation plate 140a. The first vertical board 150a may be formed to face the first heat-dissipation plate 140a.

The second vertical board 150b may be disposed in an inside of the second heat-dissipation plate 140b. The second vertical board 150b may be formed to face the second heat-dissipation plate 140b. The first vertical board 150a and the second vertical board 150b may be formed in positions in which they are symmetrical with each other based on the center in an inside of the ultrasonic probe 1.

The vertical board 150 may output signals for controlling driving of the transducer 110 by receiving signals relating to driving of the ultrasonic probe 1 from a cable connected to an inside of the ultrasonic probe 1 through a cable connection portion 180 of the lower housing 13. The vertical board 150 may include a circuit board on which chips for controlling driving of the ultrasonic probe 1 are mounted. The vertical board 150 may be formed to be electrically connected to the connection member 121 at one side of an upper portion of the vertical board 150. Thus, the vertical board 150 may be formed to be electrically connected to the transducer 110 through an FPCB and to output signals to the transducer 110.

Although not shown, the vertical board 150 may be configured so that one side of the vertical board 150 may be coupled to the heat-dissipation plate 140. Thus, the vertical board 150 may move generated heat toward the outside of the ultrasonic probe 1 through the heat-dissipation plate 140.

The ultrasonic probe 1 may further include a heat pipe 160. The heat pipe 160 may be configured so that one side of the heat pipe 160 may be connected to the heat spreader 130 and the other side of the heat pipe 160 may be coupled to a heat sink 170 that will be described later. In detail, the heat pipe 160 may be configured so that one side of the heat pipe 160 may be inserted into the insertion groove 137 of the heat spreader 130 and the other side of the heat pipe 160 may be inserted into an insertion groove 172 of the heat sink 170. The heat pipe 160 may thermally connect the heat spreader 130 and the heat sink 170 and may move heat of the heat spreader 130 toward the heat sink 170.

Figure 8:
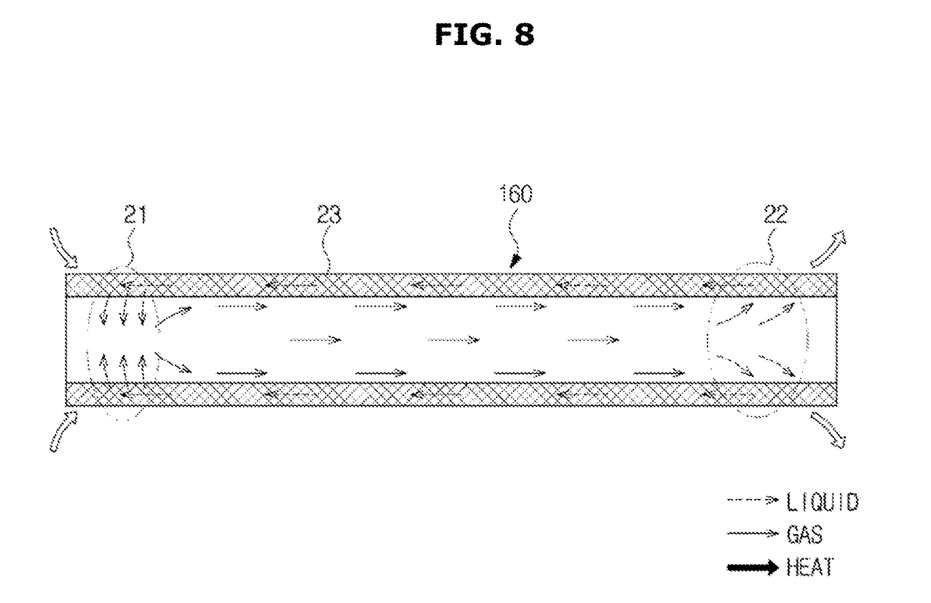
FIG. 8 is a view illustrating an operation principle of a heat pipe of FIG. 2.

FIG. 8 is a view of an operation principle of a heat pipe of FIG. 2.

The heat pipe 160 is a unit that injects a working fluid into a container having a sealed pipe shape and makes the container be in a vacuum state.

The working fluid in the heat pipe 160 exists in two phases and transfers heat.

Referring to FIG. 8, when heat is applied to an evaporation portion 21 of the heat pipe 160, heat is transferred to an inside of the heat pipe 160 due to thermal conduction through outer walls of the evaporation portion 21.

Evaporation of the working fluid occurs in the surface of a fine structure (wick) 23 at a low temperature inside the heat pipe 160 under a high pressure condition.

Due to evaporation of the working fluid, gas density and pressure of the evaporation portion 21 are increased so that a pressure gradient may be formed in a direction of a condensation portion 22 under relatively low gas density and pressure conditions on a gas path of a center of the evaporation portion 21 and a gas may move.

In this case, the moved gas moves with heat as much as latent heat of evaporation.

The gas that moves toward the condensation portion 22 is condensed on inner walls of the condensation portion 22 having a relatively low temperature, dissipates heat, and returns to its liquid state.

The working fluid returning to the liquid state moves toward the evaporation portion 21 through pores inside the fine structure 23 due to capillary pressure or gravity of the fine structure 23.

This procedure is repeatedly performed so that heat transfer may be continuously performed.

Referring again to FIGS. 2 through 7, the ultrasonic probe 1 may further include the heat sink 170. The heat sink 170 may be disposed on a lower end, i.e., a second end, of the ultrasonic probe 1 inside the ultrasonic probe 1. The heat sink 170 may be formed of a metal having excellent thermal conductivity. From the heat sink 170, heat generated in the transducer 110 and the PCB 120 may be moved through the heat-dissipation plate 140 and heat pipe 160 which are described above in detail.

A communication hole 171 through which the cable connected to the inside of the ultrasonic probe 1 using the cable connection portion 180 passes, may be formed in the heat sink 170. Also, the insertion groove 172 into which the heat pipe 160 is inserted, may be formed in the heat sink 170.

The cable connection portion 180 may include a strain relief. The cable connection portion 180 may include a material having excellent thermal conductivity. Thus, heat of the heat sink 170 may be moved toward an outside area of the lower housing 13 and dissipated.

As described above, in accordance with exemplary embodiments, heat generated in an ultrasonic probe can be effectively dissipated to the outside.

In addition, in accordance with the exemplary embodiments, stability and manufacturing facilitation of the ultrasonic probe can be improved.

While exemplary embodiments have been particularly shown and described above, it would be appreciated by those skilled in the art that various changes may be made therein without departing from the principles and spirit of the inventive concept, the scope of which is defined in the following claims.

What is claimed is:

1. An ultrasonic probe comprising:
    a housing having an opening provided at a first end portion of the housing;
    a transducer provided in a position corresponding to the opening and configured to generate ultrasonic waves;
    a heat spreader provided underneath the transducer; and
    a printed circuit board (PCB) disposed between the transducer and the heat spreader,
    wherein the heat spreader comprises:
        a body portion configured to absorb heat from the transducer; and
        a coupling portion that is formed at a side portion of the body portion and coupled to the housing.

2. The ultrasonic probe of claim 1, wherein the heat spreader further comprises a support portion that is formed proximate to the coupling portion and configured to support the PCB.

3. The ultrasonic probe of claim 1, wherein the housing comprises:
    an upper housing in which the opening is formed; and
    a lower housing coupled to the upper housing,
    wherein the coupling portion is coupled to the upper housing.

4. The ultrasonic probe of claim 3, wherein the upper housing comprises a hanging portion provided inside of the upper housing and contacting a first surface of the PCB.

5. The ultrasonic probe of claim 4, wherein the hanging portion is provided in a position corresponding to an edge portion of the PCB and has a stepped shape.

6. The ultrasonic probe of claim 1, wherein the heat spreader further comprises a protrusion that protrudes from a top surface of the body portion toward the transducer, and
    the protrusion is configured to be inserted into a connection hole formed in the PCB in a position corresponding to the protrusion.

7. The ultrasonic probe of claim 6, wherein the protrusion is spaced apart from a lower surface of the transducer by a predetermined distance.

8. The ultrasonic probe of claim 7, wherein thermal grease or a phase change material is provided between the protrusion and the transducer.

9. The ultrasonic probe of claim 1, further comprising:
    a heat sink provided at a second end portion of the housing and configured to dissipate heat to an exterior of the ultrasonic probe; and
    a heat pipe which connected to the heat spreader at a first end and to the heat sink at a second end opposite to the first end, and is configured to transfer the heat between the heat spreader and the heat sink.

10. The ultrasonic probe of claim 1, wherein the ultrasonic probe further comprises:
    a heat-dissipation plate coupled to a first side of the heat spreader; and
    a vertical board disposed in an inside of the heat-dissipation plate and coupled to a second side of the heat spreader.

11. The ultrasonic probe of claim 10, wherein the ultrasonic probe further comprises a connection member configured to electrically connect the PCB to the vertical board.

12. The ultrasonic probe of claim 11, wherein the connection member comprises a flexible PCB (FPCB).

13. The ultrasonic probe of claim 11, wherein the heat-dissipation plate comprises:
    a heat-dissipation plate body spaced apart from the vertical board by a predetermined distance; and
    a heat-dissipation plate coupling portion that extends from opposite sides of the heat-dissipation plate body toward the transducer and is coupled to the second side of the heat spreader,
    wherein a top end of the heat-dissipation plate body is disposed in a lower position than that of the connection member, with respect to the transducer.

14. The ultrasonic probe of claim 13, wherein a top end of the heat-dissipation plate coupling portion comprises a rounded shape.

15. The ultrasonic probe of claim 9, further comprising a cable connection portion which is connected to the second end portion of the housing and has a space provided therein,
    wherein the cable connection portion comprises a strain relief.

16. The ultrasonic probe of claim 15, wherein the strain relief is connected to the heat sink and comprises a thermally conductive material.

17. The ultrasonic probe of claim 1, wherein:
    the coupling portion that is formed at a side portion of the body portion is directly coupled to the housing.

18. An ultrasonic probe comprising:
    a housing having an opening provided at a first end portion of the housing;
    a transducer provided in a position corresponding to the opening and configured to generate ultrasonic waves;
    a heat spreader provided underneath the transducer and configured to absorb heat generated in the transducer;
    a heat-dissipation plate coupled to a first side of the heat spreader; and
    a vertical board that is disposed inside of the heat-dissipation plate and coupled to a second side of the heat spreader.

19. The ultrasonic probe of claim 18, further comprising a printed circuit board (PCB) and a connection member configured to electrically connect the PCB and the vertical board,
    wherein the heat-dissipation plate comprises:
    a heat-dissipation plate body spaced apart from the vertical board by a predetermined distance; and
    a heat-dissipation plate coupling portion that extends from opposite sides of the heat-dissipation plate body toward the transducer and is coupled to the second side of the heat spreader, and
    wherein a first end of the heat-dissipation plate body is disposed in a lower position than that of the connection member, with respect to the transducer.

20. The ultrasonic probe of claim 18, further comprising a cable connection portion which is connected to a second end portion of the housing and has a space provided therein,
   wherein the cable connection portion comprises a strain relief.

21. The ultrasonic probe of claim 20, further comprising:
   a heat sink that is provided at the second end portion of the housing and configured to dissipate heat to an exterior of the ultrasonic probe; and
   a heat pipe which is connected to the heat spreader at a first end and to the heat sink at a second end opposite to the first end, and is configured to transfer the heat between the heat spreader and the heat sink.

22. The ultrasonic probe of claim 18, wherein the heat-dissipation plate comprises a heat-dissipation plate body and a heat-dissipation plate coupling portion, and
   the heat-dissipation plate body faces and is substantially parallel to the vertical board.

* * * * *